(12) United States Patent
Wakino et al.

(10) Patent No.: US 7,180,307 B2
(45) Date of Patent: Feb. 20, 2007

(54) COAXIAL PROBE

(75) Inventors: Kikuo Wakino, Kyoto (JP); Toshihide Kitazawa, Kusatsu (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 457 days.

(21) Appl. No.: 10/862,464

(22) Filed: Jun. 8, 2004

(65) Prior Publication Data

US 2005/0027335 A1  Feb. 3, 2005

(30) Foreign Application Priority Data

Jul. 28, 2003 (JP) ............................. 2003-202659
May 14, 2004 (JP) ............................. 2004-145186

(51) Int. Cl.
*G01R 27/08* (2006.01)
(52) U.S. Cl. .................... 324/690; 324/693; 324/754
(58) Field of Classification Search ................ 324/690, 324/693, 754
See application file for complete search history.

(56) References Cited

U.S. PATENT DOCUMENTS 5,358,515 A * 10/1994 Hurter et al. ............... 607/101
6,813,515 B2 * 11/2004 Hashimshony ............. 600/547
2006/0155270 A1 * 7/2006 Hancock et al. ............ 606/33

FOREIGN PATENT DOCUMENTS

JP        07-275247        10/1995

* cited by examiner

*Primary Examiner*—Walter Benson
(74) *Attorney, Agent, or Firm*—Keating & Bennett, LLP

(57) ABSTRACT

A coaxial probe includes an inner conductor, an outer conductor, and a dielectric interposed between the inner and outer conductors, the top-end portion of the coaxial probe having a substantially circular cone shape between the top-end of the inner conductor and the end of the outer conductor so that a portion of the inner conductor and a portion of the dielectric are exposed, and the height of the substantially circular cone portion being set at a value at which a reflection coefficient exhibits substantially a minimum value. The dielectric constant of the dielectric is preferably within the range of about 0.132 times to about 0.6 times as large as the dielectric constant of a surrounding substance (living tissue, i.e., an object to which an electromagnetic wave is irradiated).

5 Claims, 7 Drawing Sheets

⟨POLYTETRAFLUOROETHYLENE $\varepsilon$ =2.1⟩ a: DIELECTRIC CONSTANT 43
b: DIELECTRIC CONSTANT 16
c: DIELECTRIC CONSTANT 9

⟨ALUMINA CERAMIC $\varepsilon$ =9.7⟩ a: DIELECTRIC CONSTANT 43
b: DIELECTRIC CONSTANT 16
c: DIELECTRIC CONSTANT 9

COAXIAL PROBE

BACKGROUND OF THE INVENTION

1. Field of the Invention

The present invention relates to a coaxial probe which can be introduced into a living tissue or the like to carry out heat-treatment using microwaves.

2. Description of the Related Art

Recently, for treatment of diseases such as malignant tumors or the like, several therapies using electromagnetic waves have been developed. One of the therapies is a generally known coagulation therapy which is carried out using a coaxial probe.

According to the coagulation therapy, the coaxial probe is inserted directly into the affected part of a patient. The affected part is heated directly using electromagnetic waves radiated from the coaxial probe, so that the tissue in the affected part is coagulated so as to be killed off.

Referring to methods of inserting coaxial probes into affected parts, e.g., for livers, puncturing in an incised abdomen, puncturing through the skin, insertion into the guide probe of a throracoscope or caparoscope, and so forth are known. In the above-described coagulation therapy using the coaxial probe, the incised part is relatively small, and the time required for the treatment is relatively short. Thus, advantageously, when a patient is operated, the burden to him or her can be reduced.

FIGS. 5A and 5B show the structure of a known coaxial probe (e.g., see Japanese Unexamined Patent Application Publication No. 7-275247). FIG. 5A is a longitudinal cross-sectional view of the coaxial probe 100 inserted into a schematically-shown organ such as a liver or the like. FIG. 5B is a cross-sectional view of the coaxial probe taken in the plane perpendicular to the longitudinal direction of the coaxial probe 100. As shown in FIGS. 5A and 5B, a dielectric 2 is interposed between an inner conductor 1 and an outer conductor 3. The outer conductor 3 and the inner conductor 1 are electrically connected to each other via the top end portions thereof. A slit S is formed in a part of the outer conductor 3.

FIG. 7 is a longitudinal cross-sectional view showing the structure of the top-end portion of the coaxial probe described in Patent Document 1. A microwave antenna portion 67 (the slit S shown in FIG. 5A) is provided near the end-portion of a coaxial probe cable 66. The coaxial cable 66 is inserted into a sleeve which is divided into an insertion portion 61 and a top-end portion 62. A top-end chip 63 is fixed to the end of the top-end portion 62. Thus, the coaxial probe which can be used in puncturing is formed.

Specifically, the sizes (unit: mm) of the known coaxial probe are entered in FIGS. 5A and 5B. The coaxial probe having the above-described structure and size was simulated by a computer. The reflection coefficient was 0.65. In other words, about 65% of input signals were reflected toward the input side. Thus, the known coaxial probe has problems in that the radiation efficiency with respect to electromagnetic waves is low.

Moreover, the radiation pattern of the coaxial probe was measured. FIG. 6 shows the results. In FIG. 6, the position (unit: mm) of the coaxial probe is plotted as the abscissa, in which the top-end position of the coaxial probe is taken as zero. The distance (unit: mm) in the radial direction is plotted as the ordinate. SAR (Specific Absorption Rate) is shown in graded concentrations. SAR represents the energy-quantity of an electromagnetic wave absorbed in a living body, and is used for the evaluation of the energy quantity. SAR represents the energy per unit time absorbed in unit mass in a unit of W/kg. In FIG. 6, the one step of the graded concentrations is equivalent to 2.5 dB. As seen in FIG. 6, SAR becomes high in the vicinity of the slit S. Thus, the affected part is heated in the vicinity of the slit S.

In the case of the known coaxial probe, the slit S is provided at a position that is spaced from the top end of the coaxial probe 100 (10 mm in the example shown in FIGS. 5A and 5B). Thus, the known coaxial probe cannot be conveniently used. In particular, the coaxial probe is partially passed through an affected part to be heated so that the slit of the coaxial probe is positioned in the center of the affected part. Thus, the known coaxial probe has problems in that the insertion degree (the degree at which the coaxial probe is inserted into a normal tissue) of the coaxial probe increases or the area of an affected part which can be treated becomes small.

However, if the slit is positioned near the top end of the coaxial probe improperly, the radiation efficiency cannot be enhanced, since the reflection coefficient decreases as described above.

Moreover, regarding the known coaxial probe in which the top-end chip 63 is fixed to the top-end of the coaxial probe, so that the puncturing of a living body can be realized as shown in FIG. 7, the top-end chip is large in size, and probably, the chip perforates an affected part, thus damaging a normal tissue.

SUMMARY OF THE INVENTION

In order to overcome the problems described above, preferred embodiments of the present invention provide a coaxial probe of which the radiation efficiency with respect to an electromagnetic wave is greatly improved, and SAR is increased near the top-end of probe, and with which puncturing in a living body can be easily carried out while damage to a normal tissue is minimized.

According to a preferred embodiment of the present invention, a coaxial probe includes an inner conductor, an outer conductor, and a dielectric interposed between the inner conductor and the outer conductor, a top-end portion of the coaxial probe having a substantially circular cone shape between a top-end portion of the inner conductor and the end of the outer conductor so that a portion of the inner conductor and a portion of the dielectric are exposed, the height of the substantially circular cone portion being set at a value at which a reflection coefficient exhibits substantially a minimum value.

The height of the substantially circular cone portion is determined as described above. Thus, when the coaxial probe is connected to a microwave oscillator and a microwave is emitted from the coaxial probe, the reflection coefficient is reduced. Thus, the radiation efficiency for an electromagnetic wave is greatly improved. Moreover, the top-end portion of the coaxial probe preferably has a substantially circular cone configuration. Thus, the sleeve and the top-end chip of the known coaxial probe can be omitted. Thus, with the coaxial probe, damage to a normal tissue is prevented, and puncturing can be easily carried out.

Preferably, the dielectric constant of the dielectric is preferably in the range of about 0.132 times to about 0.6 times as large as the dielectric constant of a substance surrounding the coaxial probe.

Since the dielectric constant of the dielectric is determined as described above, the reflection coefficient, obtained when the coaxial probe is practically used, is reduced. Thus, the coaxial probe can be efficiently used while the reflection is suppressed corresponding to the dielectric constant of a surrounding substance such as a living tissue.

Other features, elements, characteristics and advantages of the present invention will become more apparent from the following detailed description of preferred embodiments thereof with reference to the attached drawings.

BRIEF DESCRIPTION OF THE DRAWINGS

FIG. 1A is a longitudinal cross-sectional view of the coaxial probe inserted into an organ. FIG. 1B is a cross-sectional view of the coaxial probe taken in the plane perpendicular to the longitudinal direction of the coaxial probe;

FIG. 5A is a longitudinal cross-sectional view of the coaxial probe inserted into an organ. FIG. 5B is a cross-sectional view of the coaxial probe taken in the plane perpendicular to the longitudinal direction of the coaxial probe;

DETAILED DESCRIPTION OF PREFERRED EMBODIMENTS

Figure 1:
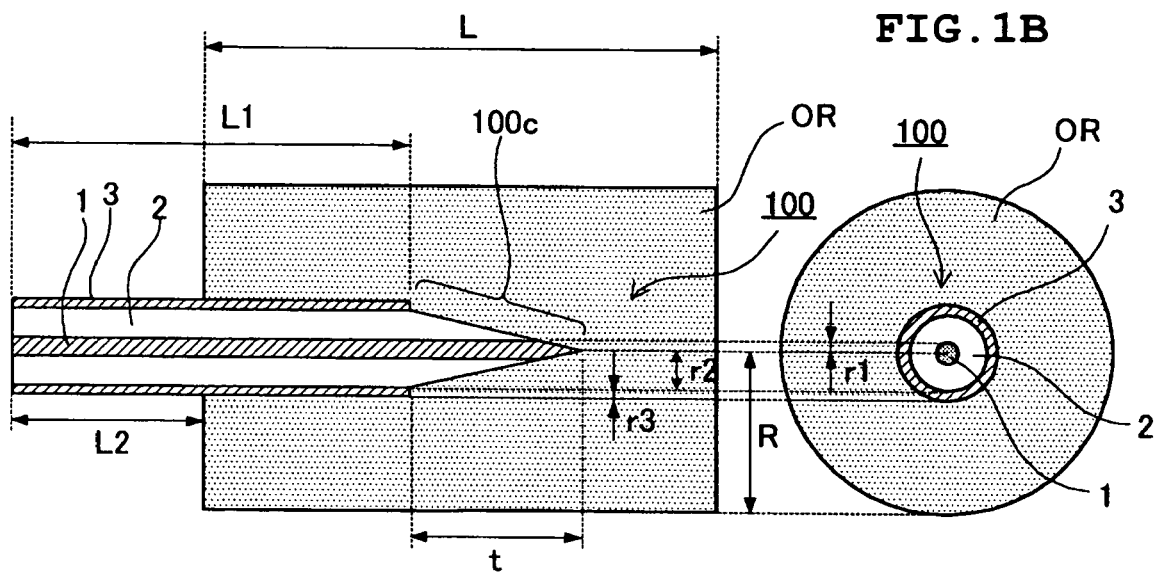
FIGS. 1A and 1B show the structure of a coaxial probe according to a first preferred embodiment of the present invention.

FIGS. 1A and 1B show the structure of a coaxial probe according to a first preferred embodiment of the present invention. FIG. 1A is a longitudinal cross-sectional view of the coaxial probe 100 inserted into an organ OR such as a liver or the like, which is schematically shown in the drawing. FIG. 1B is a cross-sectional view of the coaxial probe 100 taken in the plane perpendicular to the longitudinal direction of the coaxial probe 100. As shown in FIGS. 1A and 1B, a dielectric 2 is interposed between an inner conductor 1 and an outer conductor 3. The top-end portion of the coaxial probe 100 has a substantially circular cone shape portion 100c between the top-end of the inner conductor 1 and the end of the outer conductor 3 so that a portion of the inner conductor 1 and a portion of the dielectric 2 are exposed.

Generally, the specific absorption rate SAR with respect to a microwave irradiated to a living tissue by means of a coaxial probe, i.e., the ratio of the microwave absorbed in a unit time is determined as described below.

SAR is defined as energy absorbed by a unit-mass in a unit-time, and is expressed as W/kg. Electric power P absorbed by a unit-volume of a dielectric disposed in an electric field with a strength E is:

$$P = \omega \epsilon E^2 \tan \delta$$

in which $\epsilon$ represents the dielectric constant of a living tissue.

Electric power absorbed by a unit-mass is:

$$SAR = (\omega \epsilon E^2 \tan \delta)/\rho$$

in which $\rho$ represents the density of the living tissue.

Furthermore, $\tan \delta = \sigma/(\omega \epsilon)$ in which $\sigma$ represents the conductivity of the tissue.

Thus, the following is derived.

$$SAR = \sigma E^2/\rho.$$

Accordingly, the increase of the absorption rate with respect to an electromagnetic wave depends on the strength E of an electric field.

Figure 2:
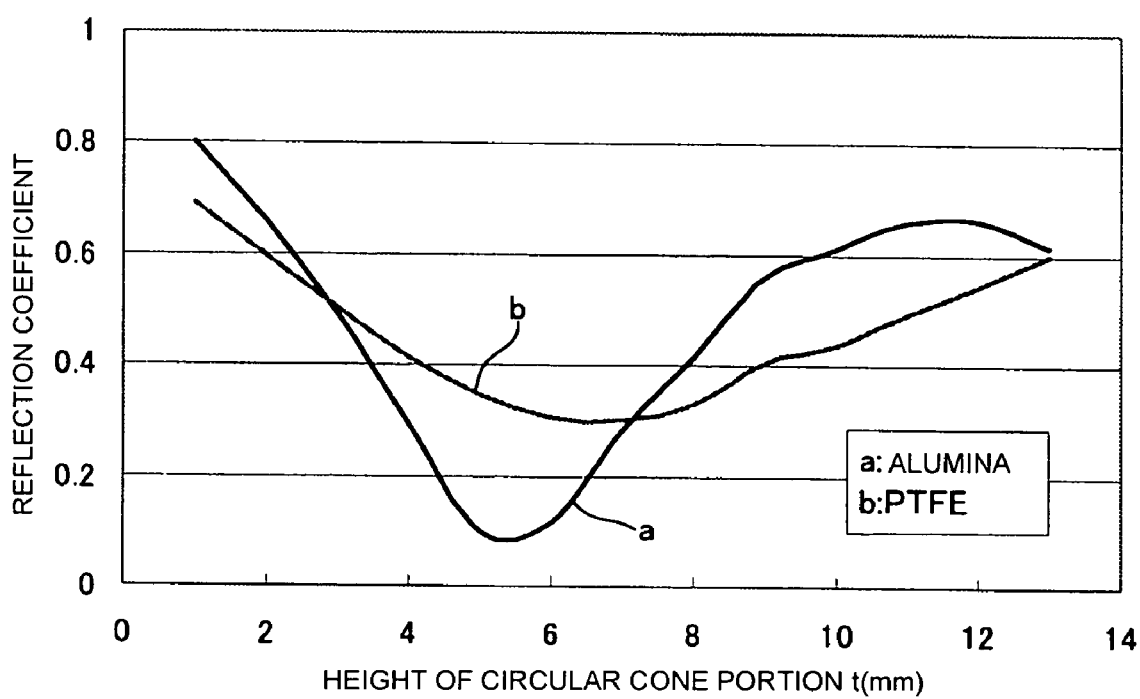
FIG. 2 shows a relationship between the height of the substantially circular cone portion of the coaxial probe and the reflection coefficient.

Regarding to the coaxial probe 100 shown in FIGS. 1A and 1B, the change of the reflection coefficient occurring when the height t of the substantially circular cone portion 100c was changed was simulated by a computer. FIG. 2 shows the results. The sizes of the respective parts of the coaxial probe shown in FIGS. 1A and 1B are listed below.

(Size of Each Part of Coaxial Probe)
L1=70 mm
L2=30 mm
r1=0.24 mm
r2=0.8 mm
r3=0.1 mm
L=60 mm
R=10 mm
(Dielectric)
(1) dielectric constant $\epsilon r$ of alumina ceramic=9.7
(2) dielectric constant $\epsilon r$ of polytetrafluoroethylene (PTFE) =2.1
(Size of Each Part of Organ OR)
L=60 mm
R=10 mm The simulation of the coaxial probe was carried out at a dielectric constant $\epsilon r$ of about 43.0 (this value is equal to the dielectric constant of a liver), tan $\delta$ of about $10 \times 10^{10}$, a conductivity $\sigma$ of about 1.69, and a frequency of about 2.45 GHz, using FEM (Finite Element Method).

As seen in the results of FIG. 2, the reflection coefficient significantly changes depending on the height t of the substantially circular cone portion. Thus, the reflection coefficient can be reduced by selection of an appropriate height t. Moreover, the height t of the substantially circular cone portion at which the smallest reflection coefficient is exhibited changes depending to the dielectric constant of the dielectric 2. For example, when the dielectric 2 is an alumina ceramic, the low reflection characteristic, i.e., the reflection coefficient of about 0.1 can be obtained at the height t of the substantially circular cone portion 100 of about 5 mm. When the dielectric 2 of polytetrafluoroethylene is used, the reflection coefficient of about 0.3 can be obtained at the height t of about 6 mm.

In ordinary cases, it is anticipated that when the height t is equal to approximately one-fourth of a guide wavelength, the potential difference between the inner conductor 1 and the outer conductor 3 becomes maximum, so that the maximum electromagnetic wave radiation can be achieved. However, the results shown in FIG. 2 depart from the above-mentioned expectation. That is, the guide wavelength of polytetrafluoroethylene is about 85 mm. The guide wavelength of alumina ceramic is about 40 mm. Therefore, the height t at which when the reflection coefficient is the smallest is not one-fourth of the guide wavelength. In both of the cases of the dielectrics of polytetrafluoroethylene and alumina ceramic, the optimum results are obtained when the height t is approximately equal to one-fourth of the wavelength (about 19 mm) of an electromagnetic wave propagating in a liver with a dielectric constant of about 43.0. In these results, it has been understood that the optimum height t of the substantially circular cone portion 100c is influenced with the dielectric constant of a living tissue surrounding the coaxial probe and the optimum height t is shifted to some degree from one-fourth of the wavelength of an electromagnetic wave propagating in the surrounding dielectric, since the dielectric constant of the dielectric of the coaxial probe exerts an influence over the optimum height t.

Figure 3:
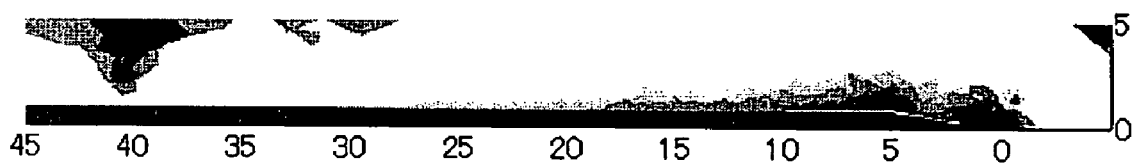
FIG. 3 shows an example of the SAR distribution of the coaxial probe.

FIG. 3 is a graph showing the SAR distribution obtained when alumina ceramic was used as the dielectric 2 of the coaxial probe, and the height t of the substantially circular cone portion 100c was about 5 mm. The position (mm) of the probe is plotted as abscissa in which the top-end position of the coaxial probe is set at zero. The distance (mm) in the radial direction of the probe is plotted as ordinate. The SAR distribution is illustrated in graded concentrations of the graph. One-step with respect to the change of the concentration is equivalent to about 2.5 dB. As seen in the above-description, the absorption ratio in the top-end portion of the coaxial probe can be considerably enhanced by setting the height t at the optimum value.

Figure 4A:
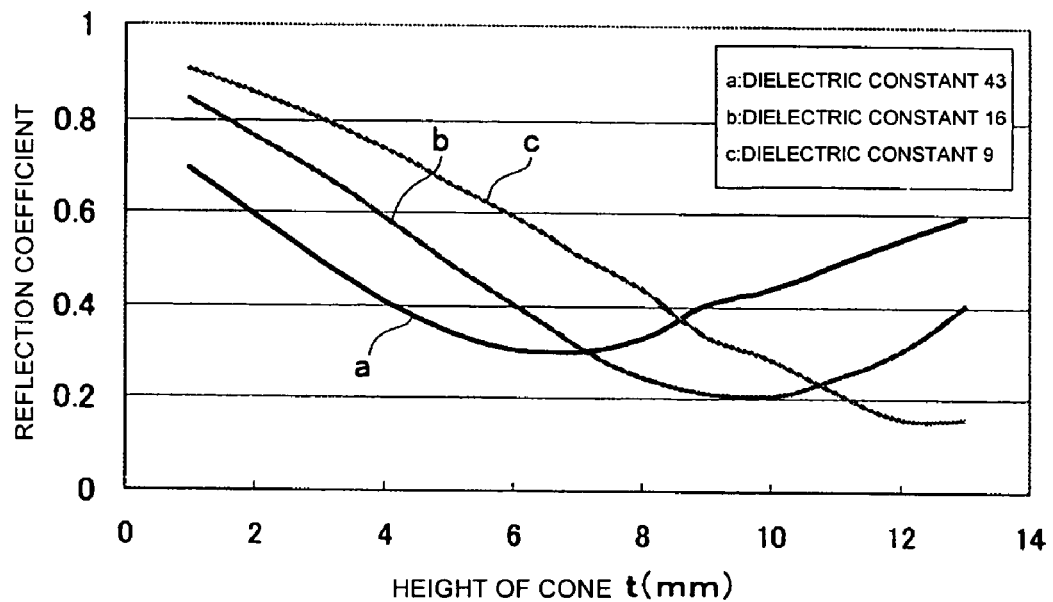
FIG. 4A is a graph showing a relationship between the height t of the substantially circular cone portion and the reflection coefficient, obtained when the dielectric constant of polytetrafluoroethylene used as a surrounding substance is changed.
Figure 4B:
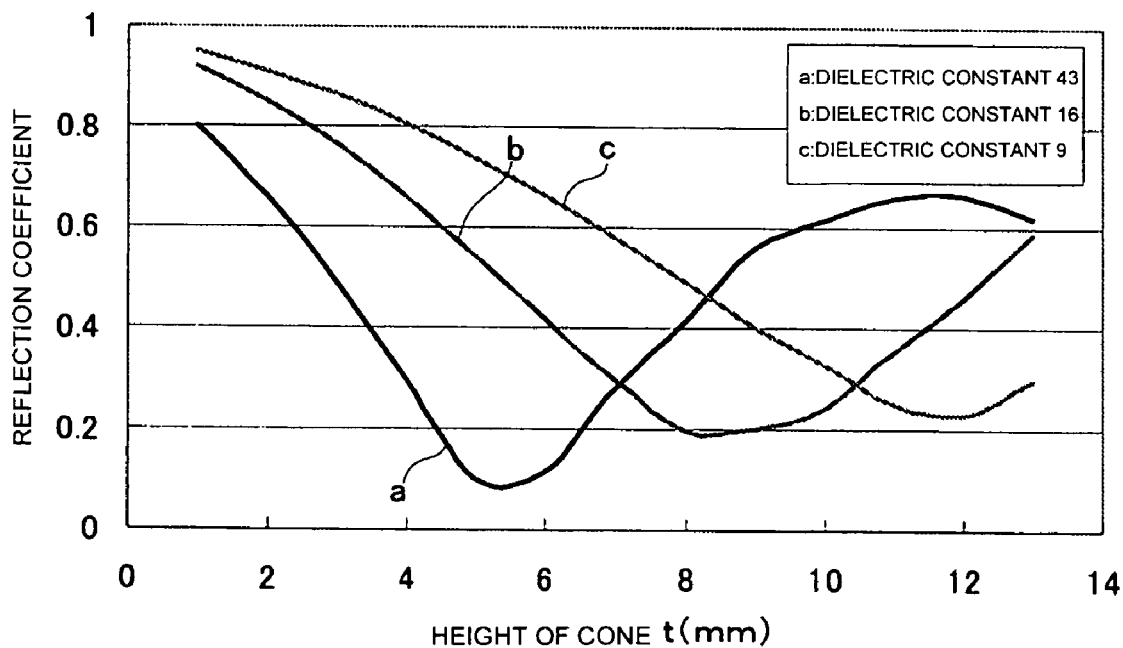
FIG. 4B is a graph showing a relationship between the height t of the substantially circular cone portion and the reflection coefficient, obtained when the dielectric constant of alumina ceramic used as a surrounding substance is changed.
Figures 5A, 5B:
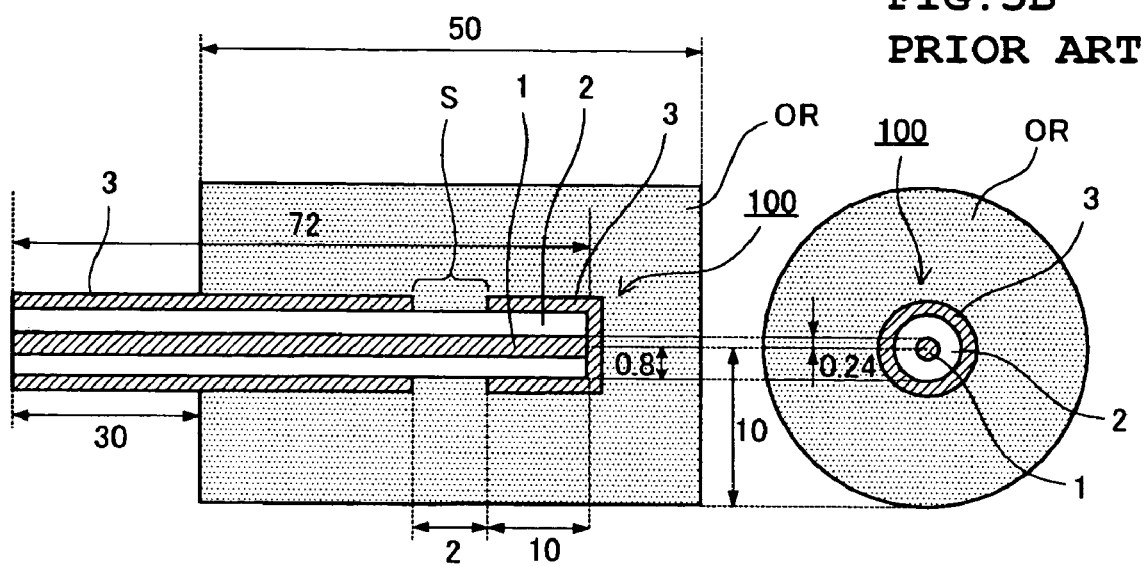
FIGS. 5A and 5B show the structure of a known coaxial probe.
Figure 6:
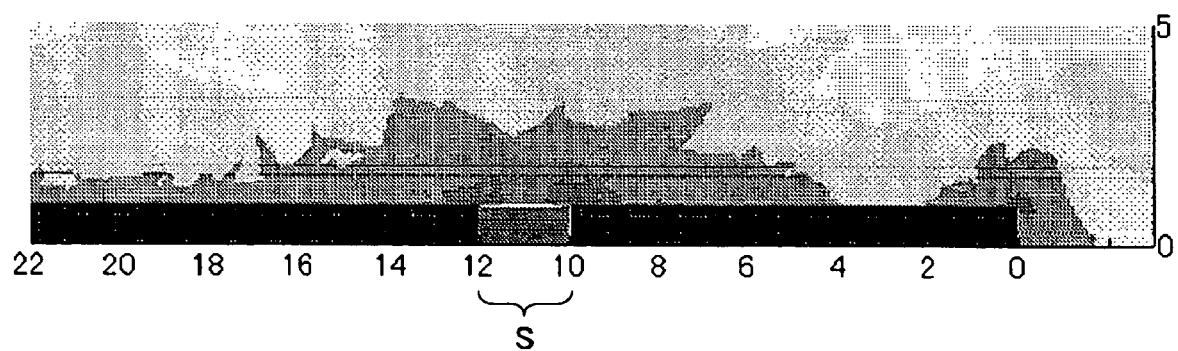
FIG. 6 shows the SAR distribution of the known coaxial probe.
Figure 7:
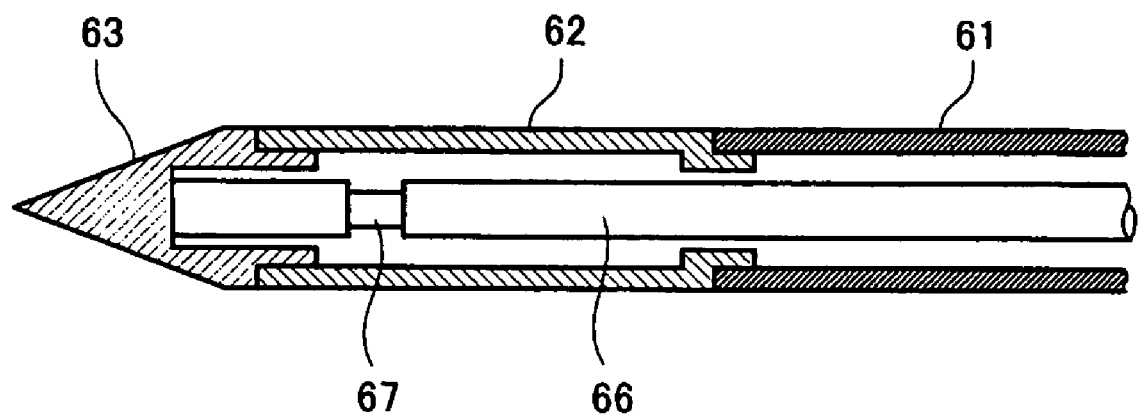
FIG. 7 is a longitudinal cross-sectional view showing the structure of the known coaxial probe.

FIGS. 4A and 4B are graphs showing the relationships between the height t of the substantially circular cone portion 100c and the reflection coefficient, obtained when the dielectric constant of a dielectric surrounding the coaxial probe was changed into three-levels. FIG. 4A is a graph showing the above-mentioned relationship, obtained when polytetrafluoroethylene was used as the dielectric 2 of the coaxial probe 100. FIG. 4B is a graph showing the above-mentioned relationship, obtained when alumina ceramic was used as the dielectric 2 of the coaxial probe 100.

The other conditions used in this simulation were the same as those described above. Regarding the surrounding substance, the tan δ and the conductivity equal to those of a liver were used.

FIGS. 4A and 4B are compared with each other. It has been shown that the reflection coefficient is strongly influenced with the dielectric constant of the surrounding substance, and moreover, the height t at which the reflection coefficient is smallest changes with the dielectric constant of the dielectric 2 existing inside the coaxial probe. Furthermore, it has been revealed that in the case of the polytetrafluoroethylene used as the dielectric 2, the reflection coefficient decreases more while the dielectric constant of the surrounding substance is reduced. Especially, it has been shown that when the dielectric constant of the surrounding substance is about 9, which is smaller than the dielectric constant of about 9.7 of the alumina ceramic, the reflection coefficient obtained when the polytetrafluoroethylene is used as the dielectric 2 is smaller than that obtained when the alumina ceramic is used as the dielectric 2. Thus, it is understood that it is effective to change the dielectric 2 of the coaxial probe 100 corresponding to the dielectric constant of a surrounding substance.

For example, in the case where the alumina ceramic is used as the dielectric 2 of the coaxial probe, the reflection coefficient is not more than about 0.2 when the dielectric constant of the surrounding substance is 16. The reflection coefficient is most favorable when the dielectric constant of the surrounding substance is about 43.0. In the case where the polytetrafluoroethylene is used as the dielectric 2 of the coaxial probe, the reflection coefficient is not more than about 0.2 when the dielectric constant of the surrounding substance is 16. The reflection coefficient is most favorable when the dielectric constant of the surrounding substance is 9. Thus, to set the reflection coefficient at about 0.2 or smaller, preferably, the ratio of the dielectric constant of the dielectric 2 of the coaxial probe 100 to that of the surrounding substance is preferably in the range of 0.132 (=2.1/16) to 0.6 (=9.7/16).

While the present invention has been described with respect to preferred embodiments, it will be apparent to those skilled in the art that the disclosed invention may be modified in numerous ways and may assume many embodiments other than those specifically set out and described above. Accordingly, it is intended by the appended claims to cover all modifications of the invention which fall within the true spirit and scope of the invention.

What is claimed is:

1. A coaxial probe comprising:
   an inner conductor;
   an outer conductor; and
   a dielectric interposed between the inner conductor and the outer conductor,
   a top portion of the coaxial probe having a substantially circular cone shape between a top of the inner conductor and an end of the outer conductor so that a portion of the inner conductor and a portion of the dielectric are exposed,
   a height of the substantially circular cone shape portion being set at a value at which a reflection coefficient exhibits substantially a minimum value.

2. A coaxial probe according to claim 1, wherein the dielectric constant of the dielectric is within a range of about 0.132 times to about 0.6 times as large as the dielectric constant of a substance surrounding the coaxial probe.

3. A coaxial probe according to claim 1, wherein the dielectric is polytetrafluoroethylene.

4. A coaxial probe according to claim 1, wherein the dielectric is alumina ceramic.

5. A coaxial probe according to claim 1, wherein the height of the substantially circular cone portion is about 5 mm.

* * * * *